(12) United States Patent
Chen et al.

(10) Patent No.: US 8,039,454 B2
(45) Date of Patent: Oct. 18, 2011

(54) MACROLIDE COMPOUNDS WITH ANTIBIOTIC AND ANTINEOPLASTIC PROPERTIES

(75) Inventors: Genhui Chen, Burnaby (CA); Bin Li, Burnaby (CA); John M. Webster, North Vancouver (CA); Kaiji Hu, Burnaby (CA); Jianxiong Li, Port Moody (CA)

(73) Assignee: Weihe Pharmaceuticals Co. Ltd., Yuxi, Yunan (CN)

( * ) Notice: Subject to any disclaimer, the term of this patent is extended or adjusted under 35 U.S.C. 154(b) by 43 days.

(21) Appl. No.: 12/084,959

(22) PCT Filed: Nov. 28, 2006

(86) PCT No.: PCT/CA2006/001934
§ 371 (c)(1),
(2), (4) Date: May 14, 2008

(87) PCT Pub. No.: WO2007/068084
PCT Pub. Date: Jun. 21, 2007

(65) Prior Publication Data
US 2009/0264644 A1 Oct. 22, 2009

(51) Int. Cl.
C07D 269/00 (2006.01)
A61K 31/33 (2006.01)
A61P 31/00 (2006.01)
A61P 35/00 (2006.01)

(52) U.S. Cl. .................. 514/183; 540/456
(58) Field of Classification Search .............. 540/456; 514/183
See application file for complete search history.

(56) References Cited

U.S. PATENT DOCUMENTS
5,294,609 A * 3/1994 Arisawa et al. ............ 514/183
* cited by examiner Primary Examiner — Bruck Kifle

(57) ABSTRACT

The invention is drawn to novel macrolide compounds of formula I having antibiotic and antineoplastic activities, useful as medicaments and/or agrochemicals for microorganism infections, in particularly for infectious diseases involving drug-resistant *Staphylococcus*, and for treatment of human and animal cancers.

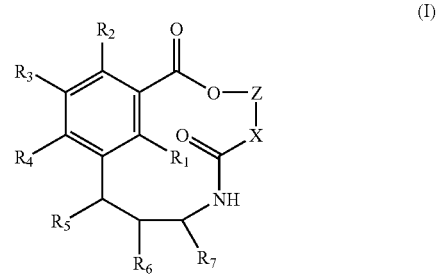

4 Claims, No Drawings

MACROLIDE COMPOUNDS WITH ANTIBIOTIC AND ANTINEOPLASTIC PROPERTIES

The present invention provides the novel compounds WBI-3001 having antibiotic and antineoplastic activities. The present invention also provides methods for the production of WBI-3001 sereis, comprising the step of cultivating the microorganism *Xenorhabdus* species. The present invention further provides antibiotic and antineoplastic compositions comprising WBI-3001, the salts thereof, and methods of using the inventive compounds as antibiotic and antineoplastic agents.

BRIEF DESCRIPTION OF THE DRAWING

The following figure represents the structural formula of WBI-3001 series, a novel group of compounds,

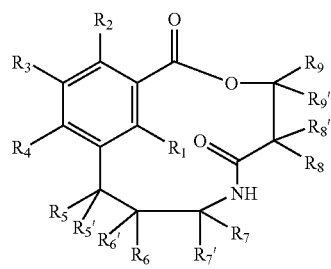

Formula I

Wherein $R_1$, $R_2$, $R_3$, $R_4$, $R_5$, $R_5'$, $R_6$, $R_6'$, $R_7$, $R_7'$, $R_8$, $R_8'$, $R_9$ and $R_9'$ are independently selected from the groups consisting of H, unsubstituted or substituted alkyl, cycloalkyl, alkenyl, alkynyl, aryl or aralkyl group, halo, nitro, CN, hydroxyl, amino, $COR_{10}$, $NR_{11}R_{12}$, $S(O)_2NR_{11}R_{12}$, $S(O)_nR_{11}$, n=0-2, $OR_{13}$, and heterocyclic group. $R_5$ and $R_5'$; $R_6$ and $R_6'$; $R_7$ and $R_7'$; $R_5$ and $R_5'$; $R_9$ and $R_9'$ can not be nitro, CN, hydroxyl, amino, $COR_{10}$, $NR_{11}R_{12}$, $S(O)_2NR_{11}R_{12}$ simultaneously.

$R_{10}$ is selected from H, unsubstituted or substituted alkyl, cycloalkyl, aryl, or aralkyl, or $NR_{11}R_{12}$, or $OR_{11}$;

$R_{11}$ and $R_{12}$ are selected from H, unsubstituted or substituted alkyl, cycloalkyl, aryl or aralkyl;

$R_{13}$ is selected from H, unsubstituted or substituted alkyl, cycloalkyl, aryl, aralkyl or acyl.

BACKGROUND

It has become increasingly apparent in recent years that the problems of pests and diseases of man, domestic animals and crops that were once controlled by the use of synthetic pesticides and chemotherapeutic agents have re-emerged in many parts of the world, due to social, legislative and biological change. In both medicine and agroforestry, the development of resistance to pesticides and chemotherapeutic drugs in many micro-organisms is becoming progressively more challenging to humans. As well, treatment of human and animal neoplastic diseases remains to be a great task. There is, therefore, an urgent need for new agrochemicals and new drugs to control diseases effectively. The diversity of microbial products from soil inhabiting microorganisms has been a traditional source for the discovery of new pharmaceuticals and agrochemicals.

One of the recent developments has been the commercialization of a nematode-bacteria combination as biological control agents against insect pests. A crucial feature of this biocontrol agent is that the bacterial symbiont (*Xenorhabdus* spp. or *Photorhabdus* spp.) of the nematode produces a wide range of bioactive metabolites including antimicrobial substances that inhibit the growth of bacteria, fungi and yeasts (Webster et al., 2002).

Although there are a limited number of publications on this aspect of the biology of *Xenorhabdus* spp. and *Photorhabdus* spp., it has been recognized that bioactive substances are produced by these bacteria. Some of these specific compounds have been isolated, identified and their structures elucidated (Forst and Nealson, 1996). Recently, the cell-free culture broths of *Xenorhabdus* species and *Photorhabdus luminescens* were found to be active against many fungi of agricultural and medicinal importance (Chen et al., 1994). Two new classes of antimicrobial substances, nematophin (Webster et al., U.S. Pat. No. 5,569,668) and xenorxides (Webster et al., U.S. Pat. No. 6,316,476), were found from these bacterial cultures. As well, xenorxides have been shown to have very strong antineoplastic activity (Webster et al., U.S. Pat. No. 6,020,360). As part of the ongoing investigation of these bacteria, the WBI-3001 series, a novel group of chemicals have been found to have extremely potent antibiotic and antineoplastic activities and are the subjects of this invention, Prior art references have not shown the existence of WBI-3001 and the use of WBI-3001 or any operable aspects as antibiotic and/or antineoplastic agents.

DETAILED DESCRIPTION OF THE INVENTION

The Microorganisms

*Xenorhabdus bovienii* and its nematode symbiont *Steinernema feltiae* used in this study were collected from soil in British Columbia, Canada and maintained in culture in Dr. J. M. Webster's laboratory in the Department of Biological Sciences, Simon Fraser University, Burnaby, B.C., Canada V5A 1S6. Briefly, last instar larvae of the Greater Wax Moth, *Galleria mellonella*, were infected with infective juvenile (IJ) nematodes, carrying the *X. bovienii* A21 strain, at a rate of 25 IJs/larvae. After 24 to 48 h the dead insect larvae were surface disinfected by dipping them into 95% EtOH and igniting them. The cadavers were aseptically dissected, haemolymph was streaked onto an agar culture medium and incubated in the dark at room temperature. The bacterial strain from which the compounds of this invention were isolated was deposited under the Budapest Treaty in the American Type Culture Collection, Rochville, Md. with a designation number of ATCC 55743. The procedure of isolation and the characteristics of this bacterial strain are fully described in Webster et al., U.S. Pat. No. 6,583,171.

Production of WBI-3001

Cultivation of the microorganism *X. bovienii* yields the novel substances, WBI-3001. To prepare WBI-3001, *X. bovienii* may be cultivated (fermented), for example, at about 25° C. under submerged, aerobic conditions in an aqueous, nutrient medium containing assimilable carbon (carbohydrate) and nitrogen sources until antibiotic activity due to WBI-3001 is imparted to the medium. The fermentation may be carried out for a time period such as approximately 48 to 96 hours, at the end of which time the antibiotic WBI-3001 have been formed, and may be isolated from the fermentation medium and purified.

After the fermentation has been completed, the fermented broth may be filtered or centrifuged and the pH of the filtrate adjusted to about 7.0 by the addition of hydrochloric acid or kept as it was. The filtrate may then be extracted with a water immiscible organic solvent, for example, with ethyl acetate or chloroform. The combined organic layers (e.g. pooled ethyl acetate or chloroform extracts) may be concentrated under vacuum (e.g. at about 30° C.) to an oily residue ("syrup"). The oil may be mixed with a small amount of organic solvent and chromatographed on a silica gel column. After introduction of the sample, chloroform or other organic solvent may be applied to elute the bioactive fraction. The bioactive fraction may be purified further by high performance liquid chromatography (HPLC) with organic and/or aqueous solution.

The compounds of the present invention include WBI-3001 and salts thereof. The term "salts", as used herein, denotes acidic and/or basic salts, formed with inorganic and/or organic acids and bases. Suitable acids include, for example, hydrochloric, sulfuric, nitric, benzeenesulfonic, acetic, maleic, tartaric and the like which are pharmaceutically acceptable. While pharmaceutically acceptable salts are preferred, particularly when employing the compounds of the invention as medicaments, other salts find utility, for example, in processing these compounds, or where non-medicament-type uses are contemplated.

The WBI-3001 and Use Thereof

As WBI-3001 possess antibiotic activity against microorganisms pathogenic to animals and plants, they can be used for the treatment and prophylaxis of infections caused by such organisms, particularly, infection caused by antibiotic-resistant bacteria such as bacteria of the genus of *Staphylococcus*. Hosts treatable include plants and animals, particularly mammals such as dogs, cats and other domestic animals and, especially, humans.

WBI-3001 has also strong antineoplastic activity against several human cancer cell lines. Most importantly, WBI-3001 inhibited the growth of human lung cancer as well as the growth of human cervical and breast cancers.

The dosage form and mode of administration, as well as the dosage amount, may be selected by the skilled artisan. Exemplary daily dosages for an adult human are those within the range of about 2.5 mg to about 2,000 mg/day. Administration to a mammalian host may, for example, be oral, parenteral, or topical. Administration to a plant host may be accomplished, for example, by application to seed, foliage or other plant part, or to the soil.

When WBI-3001 or the salts thereof are used as therapeutics, they can be administrated alone or in a pharmaceutically suitable formulation containing, in addition to the active ingredient, one or more conventional carrier. Depending on the nature of the disease and/or route of administration, the composition of this invention can be formulated by known means.

Examples of pharmaceutical compositions include any solid (tablets, pills, capsules, granules, powder etc.) or liquid (solutions, suspensions or emulsions) compositions suitable for oral, topical or parenteral administration, and they may contain the pure compound or a salt thereof or in combination with any carrier or other pharmaceutically active compounds. These compositions may need to be sterile when administered parenterally.

The dosage administered will depend upon the identity of the diseases, the type of host involved including its age, health and weight; the kind of concurrent treatment, if any; and the frequency of treatment and therapeutic ratio. Illustratively, dosage levels of the administered active ingredients are intravenous, 0.1 to about 200 mg/kg; intramuscular, 1 to about 500 mg/kg; orally, 5 to about 1000 mg/kg; intranasal instillation, 5 to about 1000 mg/kg; and aerosol, 5 to about 1000 mg/kg of host body weight. Expressed in terms of concentration, an active ingredient can be present on the compositions of the present invention for localized use about the cutis, intranasally, pharyngolaryngeally, bronchially, intravaginally, rectally, or ocularly in a concentration of from about 0.01 to about 50% w/w of the composition, preferably about 1 to about 20% w/w of the composition. Also, similarly for parenteral use the invention can be used in a concentration of from about 0.05 to about 50% w/v of the composition and preferably from about 5 to about 20% w/v. The WBI-3001 or the salts thereof, used as active ingredients to be employed as antibiotic and/or antineoplastic agents for treatment of animal and human illness can be easily prepared in such unit dosage form with the employment of pharmaceutical materials which themselves are available in the art and can be prepared by established procedures. The appropriate solid or liquid vehicle or diluent may be selected, and the compositions prepared, by methods known to the skilled artisan.

For agricultural application, the antibiotic compositions may be formed using one of the active ingredients in an inert carrier. If formulated as a solid, the ingredients may be mixed with typical carriers such as Fuller's earth, kaolin clays, silicas or other wettable inorganic diluents. Free-flowing dust formulations may also be utilized by combining the dry active ingredient with finely divided solids such as talc, kieselguhr, pyrophyllite, clays, diatomaceous earth and the like.

The powders may also be applied as a suspension or solution, depending on the solubility in the liquid carrier. Pressurized sprays, typically aerosols with the active ingredient dispersed in a low-boiling dispersant solvent carrier, may be used. Percentages of weight may vary according to the manner in which the composition is to be applied, and formulation used. In general, the active ingredient will comprise 0.005% to 95% of the active ingredient by weight in the antibiotic composition. The antibiotic composition may be applied with other ingredients, including growth regulators, insecticides, fertilizers, and the like. Formulation of the active ingredients to assist applicability, ease handling, maintain chemical stability and increase effectiveness may require addition of various materials. Solvents may be chosen on the basis of affecting the solubility of the active ingredient, fire hazard and flash point, emulsifiability, specific gravity and economic considerations. Adjuvants may be added to enhance the active ingredients, and can include surfactants which are anionic, cationic or nonionic. Stabilizers and antifreeze compounds will prolong storage. Additionally, synergists, stickers, spreaders and deodorant compounds can be added to improve the handling characteristics of the commercial formulation. Alternatively, the active ingredient can be combined with an inert carrier, such as calcium carbonate, and formed into a pill or other consumable delivery device, including controlled release devices intended to deliver metered doses of the active ingredient.

The inventive compounds may be employed also as antibiotic agents useful in inhibiting the growth of microorganisms present or eradicating microorganisms on a surface or in a medium outside a living host. The inventive compounds and/or their salts thereof may be employed, for example, as disinfectants for a variety of solid and liquid media susceptible to microbial growth. Suitable amounts of the inventive compounds may be determined by methods known to the skilled artisan.

The following examples are provided to further illustrate the invention, and are not intended to in any way limit the scope of the instant claims.

Example 1

Production and Isolation of WBI-3001 from the Culture Broth of *X. bovienii*

The primary form of *X. bovienii* was maintained and subcultured at 14 d intervals. Inocula of the primary form were prepared by adding one loopful of the culture to 50 ml of tryptic soy broth (TSB) in a 100 ml Erlenmeyer flask. Cultures were shaken at 120 rpm on an Eberbach gyrorotary shaker for 24 h at 25° C. Bacterial fermentation was initiated by adding 100 ml of this bacterial culture to 900 ml of TSB in a 2,000 ml flask. The flask was incubated in the dark at 25° C. on an Eberbach gyrorotary shaker. After 96 h, the culture was immediately centrifuged (12,000×g, 20 minutes, 4° C.) to separate the bacterial cells. Twenty litres of media was inoculated by X. bovienii. The inoculated media was incubated at 37° C. for 3 days. Then media was grinded and extracted with 20 L of ethyl acetate three times. Extracts were combined and evaporated under vacuum. About 20 gram of oily stuff was obtained after the evaporation. To this oily stuff, 100 ml of hexanes was added and the resulted mixture was stirred for half an hour. Solid precipitate appeared after this treatment. About 10 grams of solid was collected by filtration. The solid was redissolved in 20 ml of chloroform and loaded upon a column of silica gel for separation by chromatograph. Mixture of chloroform and methanol (9:1) was used as eluent. The separation of chemicals was test by TLC. Chemicals purified by chromatograph were submitted for antibacterial activity test. One chemical with significant antibacterial activity was found and was identified by NMR and MS. The structure of this chemical is showed as below:

Example 2

Identification of WBI-3001

NMR spectra were recorded on a Bruker WM600 spectrometer in $C_5D_5N_5$. Low resolution MS were obtained on a Hewlett-Packard 5985B gc/ms system operating at 70 eV using a direct probe. CIMS spectra were obtained with isobutane on the same instrument as described above. High resolution MS were recorded on a Kratos MS80 instrument. HPLC and UV analysis was performed on Waters 2695 with a Waters 996 PDA detector.

$^1$H NMR(C5D5N) (600 Hz) δ0.87 (dd, 6H, J=7.2 Hz), 1.42(mult., 1H), 1.83(mult., 2H), 1.92(mult., 2H), 2.21(mult., 1H), 2.35(mult., 1H), 2.94(dd, 1H, J=16 Hz, J=3 Hz), 3.21 (dd, 1H, J=16 Hz, J=13 Hz), 3.41(mult., 1H), 4.40(mult., 1H), 4.66(mult., 1H), 4.72(dd., 1H, J=16 Hz, J=3 Hz), 4.88(d, 1H, J=6 Hz), 5.02(dd, 11H, J=6 Hz, J=3 Hz), 6.62(d, 1H, J=7 Hz), 6.97(d, 1H, J=8 Hz), 7.35(t, 1H, J=8 Hz), 8.78(d, 1H, J=9 Hz).

$^{13}$C NMR(C5D5N) (600 Hz) δ21.76(C-1), 23.41(C-1'), 24.70(C-8), 24.94 (C-2), 25.91(C-7), 30.10 (C-6), 39.93(C-3), 45.53(C-12), 49.39(C-4), 62.46(C-9), 71.78(C-11), 74.16 (C-10), 81.77(C-5), 109.07(C-18), 115.95(C-20), 118.67(C-19), 136.50(C-17), 140.78(C-15), 162.40 (C-16), 170.01(C-13), 173.99(C-14).

MS: 408(CI) (M+1)

UV (CH$_3$CN:H$_2$O=2:8): Dmax (log ε) 314.8 nm (3.7).

Example 3

WBI-3001 as Antibiotic Agents

The following experiments were conducted, demonstrating the antibiotic properties of WBI-3001. To determine minimum inhibitory concentration (MIC) of the WBI-3001, the standard dilution method was used. The tests were conducted at 35° C. and the MICs were determined after 24 h incubation.

Table 1 shows the MICs determined for the compounds against each microorganism. In conclusion, it is shown that WBI-3001 isolated from *Xenorhabdus* have potent antibiotic properties, particularly against some antibiotic resistant *Staphylococcus* strains.

TABLE 1

MICs of WBI-3001 and Erythromycin in Tryptic Soy Broth at 24 hr and 48 hr time points (Note: MIC values given in units of μg/ml).

| Bacteria Sample | WBI-3001 | Erythromycin |
|---|---|---|
| *Escherichia coli* | 4 | 1 |
| *Staphylococcus epidermidis* | 8 | 0.25 |
| *S. aureus* MSRA* | 4 | >32 |
| *Enterococcus faecalis* | 32 | >32 |
| *Streptococcus pyogenes* | 4 | 0.03 |
| *Pseudomonas aeruginosa* | >32 | >32 |

*clinical isolates of methicillin-resistant strain.

Example 4

WBI-3001 as Antineoplastic Agents

The antineoplastic activities of WBI-3001 have been determined in vitro in cell cultures of human lung cancer H460, breast cancer MCF-7 and cervical cancer Hela. The tests were carried out using the method described by Skehan et al. (1990). Both WBI-3001 exhibit very strong antineoplastic activity against these cancer cells.

TABLE 2

Antitneoplastic activity of WBI-3001 in three cancer cell lines.

| | IC$_{50}$ (μg/ml) | | |
|---|---|---|---|
| Compound | H460 | MCF-7 | Hela |
| WBI-3001 | 0.1 | 0.81 | 0.24 |

While our above description contains many specificities, these should not be construed as limitations on the scope of the invention, but rather as examples of preferred embodiments. Accordingly, the scope of the invention should not be determined by the embodiments presented, but by the appended claims and their legal equivalents.

What is claimed is:

1. A compound of WBI-3100 with the structure shown below, or a pharmaceutically acceptable salt thereof

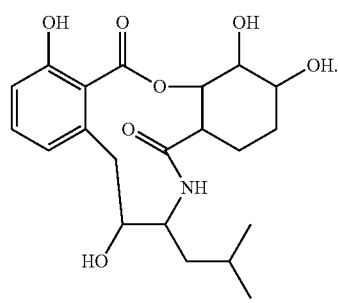

2. A pharmaceutical composition of the compound WBI-3100 with the structure shown below, or a pharmaceutically acceptable salt thereof

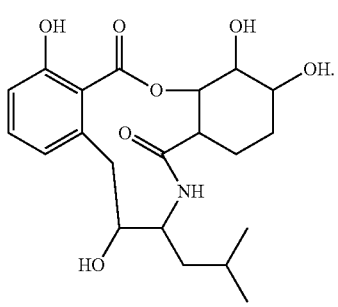

3. A method of inhibiting bacteria, comprising administrating to a subject in need of such treatment, an effective amount of a compound of claim 1 or a pharmaceutically acceptable salt thereof.

4. A method of treating human cancers of the lung, breast and cervical, comprising administrating to a subject in need of such treatment, an effective amount of the compound of claim 1 or a pharmaceutically acceptable salt thereof.

* * * * *